US 8,076,119 B2

(12) United States Patent
Floris et al.

(10) Patent No.: US 8,076,119 B2
(45) Date of Patent: Dec. 13, 2011

(54) ***BREVIBACILLUS LATEROSPORUS* STRAIN COMPOSITIONS CONTAINING THE SAME AND METHOD FOR THE BIOLOGICAL CONTROL OF DIPTERS**

(75) Inventors: Ignazio Floris, Sassari (IT); Luca Ruiu, Sassari (IT); Alberto Satta, Sassari (IT); Gavino Delrio, Alghero (IT); Salvatore Rubino, Sassari (IT); Bianca Paglietti, Sassari (IT); David John Ellar, Cambridge (GB); Roberto A. Pantaleoni, Alghero (IT)

(73) Assignee: Universita Degli Studi di Sassari, Sassari (IT)

( * ) Notice: Subject to any disclaimer, the term of this patent is extended or adjusted under 35 U.S.C. 154(b) by 312 days.

(21) Appl. No.: 12/441,457

(22) PCT Filed: Sep. 14, 2007

(86) PCT No.: PCT/EP2007/059719
§ 371 (c)(1),
(2), (4) Date: Mar. 16, 2009

(87) PCT Pub. No.: WO2008/031887
PCT Pub. Date: Mar. 20, 2008

(65) Prior Publication Data
US 2010/0003227 A1   Jan. 7, 2010

(30) Foreign Application Priority Data
Sep. 15, 2006 (IT) .............................. MI2006A1765

(51) Int. Cl.
*C12N 1/20* (2006.01)
(52) U.S. Cl. .................................................. 435/252.1
(58) Field of Classification Search .................... None
See application file for complete search history.

(56) References Cited

FOREIGN PATENT DOCUMENTS
WO   WO 2007/147096   12/2007

OTHER PUBLICATIONS

De Oliveira et al., "Molecular Characterization of *Brevibacillus laterosporus* and its Potential Use in Biological Control," Applied and Environmental Microbiology 70:6657-6664, 2004.
Favret et al., "Insecticidal Activity of *Bacillus laterosporus*," J. Invertebrate Pathology 45:195-203, 1985.
Laubach et al., "Studies on Aerobic Spore-Bearing Non-Pathogenic Bacteria," The Laboratory of Hygiene and Bacteriology, Johns Hopkins University, 1:505-533, 1916.
McCray, "Spore-Forming Bacteria of the Apiary," J. Agricultural Res. 8:399-423, 1917.
Orlova et al., "Insecticidal Activity of *Bacillus laterosporus*," Applied and Environmental Microbiology 64:2723-2725, 1998.
Rivers at al., "Mosquitocidal Activity of *Bacillus laterosporus*," J. Invertebrate Pathology 58:444-446, 1991.
Ruiu at al., "Lethal and Sublethal Effects of *Brevibacillus laterosporus* on the Housefly (*Musca domestica*)," Entomologia Experimentalis et Applicata 118:137-144, 2006.
Singer, "The Utility of Morphologica Group II *Bacillus*," Advances in Applied Microbiology 42:219-261, 1996.
Smirnova et al., "The Crystal-Forming Strains of *Bacillus laterosporus*," Res. Microbiol. 147:343-350, 1996.
International Search Report from International Application No. PCT/EP2007/059719, dated Feb. 21, 2008.
Written Opinion from International Application No. PCT/EP2007/059719, dated Feb. 21, 2008.
International Preliminary Report on Patentability from International Application No. PCT/EP2007/059719, dated Nov. 24, 2008.

*Primary Examiner* — Nita M Minnifield
*Assistant Examiner* — Brian J Gangle
(74) *Attorney, Agent, or Firm* — Clark & Elbing LLP

(57) ABSTRACT

The invention relates to a new bacterial strain belonging to the genus *Brevibacillus laterosporus* deposited at the NCIMB Ltd. Aberdeen, UK and to its derivatives. The bacterium and its derivatives have insecticidal activity and constitute the active principle of compositions and feeding baits used for biological control of Dipters, Nematocers and Brachycerus (flies, mosquitos, horseflies and midges) and especially against the species *Musca domestica*. Therefore, according to a further aspect, the invention relates to a method for biological control of insects belonging to the order Dipters. The active principle has activity against Nematocers and Brachycerus (flies, mosquitos, horseflies and midges) and especially against the species *Musca domestica*.

19 Claims, No Drawings

BREVIBACILLUS LATEROSPORUS STRAIN COMPOSITIONS CONTAINING THE SAME AND METHOD FOR THE BIOLOGICAL CONTROL OF DIPTERS

FIELD OF THE INVENTION

The present invention relates to a new bacterial strain used for biological control of insects, especially Dipters.

STATE OF THE ART

*Musca domestica* is an ubiquitous insect of worldwide medical-veterinary importance. Its harmfulness is due both to the nuisance caused to humans and animals, with impact on the zootechnical production, to the risks of transmission of various microorganisms that can cause enteric diseases.

Favourable levels of temperature and humidity during the spring-summer season and the abundance of substrates for development and proliferation of young stages in zootechnical environments and dumps, determine an exponential increase of the density of the fly population, thus requiring intervention and control.

Common control measures are based on the use of chemical insecticides with unavoidable negative consequences on environmental impact. The risks for the environment and for human health, together with phenomena of well known insecticide resistance in this insect support the introduction of eco-compatible control measures in the context of integrated control programs, with special focus on biological measures.

The introduction of formulations containing bacterial strains effective against *Musca domestica* has been one of the objectives pursued by several researchers, considering that similar positive results were obtained in the control of other harmful insects with the use of commercial formulates based on entomopathogenic bacteria, especially specific *Bacillus thuringiensis* strains (the major biological insecticide on the market).

*Brevibacillus laterosporus* is an aerobic bacterium characterized by the production of a typical canoe-shaped lamellar parasporal body, tightly adhering to the spore wall. This is a bacterial strain that was initially isolated in water (Laubach, 1916) and was already indicated as potential entomopathogenic agent at the beginning of the XX century due to the observation that it could be isolated in sick bees (McCray, 1917).

Only recently its insecticidal properties against mosquito larvae (*Culex quinquefasciatus* and *Aedes aegypti*) and against *Simulium vittatum* (Favret & Yousten, 1985; Rivers et al., 1991), coleopters, nematodes, molluscs (Singer, 1996) and Lepidoptera (Oliveira et al., 2004) larvae have been shown. Furthermore, some strains producing parasporal inclusions similar to those produced by *Bacillus thuringiensis* (Smirnova et al., 1996) turned out to be especially toxic against mosquito larvae (*Aedes aegypti, Anopheles stephensi* and *Culex pipiens*) (Orlava et al., 1998).

Ruiu et al. 2006 describes a strain to which *Musca domestica* larvae and adults were proven to be susceptible, showing lethal and sub-lethal effects. However this strain shows a lower level of toxicity compared to that obtainable with strain UNISS18 object of the present invention.

SUMMARY OF THE INVENTION

The invention relates to a new bacterial strain belonging to the genus *Brevibacillus laterosporus* deposited with NCIMB N° 41419 in the NCIMB Ltd. Aberdeen, UK and to its derivatives obtained by mutation or genetic transformation or by growth in selective conditions.

Products obtained by extraction, sub-cellular fractionation and/or lysis of cultures containing this bacterium are also considered *Brevibacillus laterosporus* derivatives.

According to a primary aspect of the invention, this bacterium and its derivatives with insecticidal activity constitute the active principle of compositions and feeding baits used for biological control of Dipters.

According to a further aspect, the invention relates to a method for biological control of insects belonging to the order Dipters characterized in that it uses the microorganism according to the invention or its derivatives and/or compositions according to the invention or feeding baits.

The active principle has activity against Nematocers and Brachycerus (flies, mosquitos, horseflies and midges) and especially against the species *Musca domestica*.

DETAILED DESCRIPTION OF THE INVENTION

The present study relates to the isolation from samples of soil from central Sardinia (Italy) of a new *Brevibacillus laterosporus* bacterial strain deposited on Jul. 28, 2006 with NCIMB n° 41419 (NCIMB Ltd. Ferguson Building, Craibstone Estae, Bucksburn, Aberdeen, UK, AB 21 9YA) also designated UNISS18.

Together with the present finding, the inventors have also set up a method for biological control and especially for microbiological control of Insects belonging to Dipterans, especially *Musca domestica*, by use of formulations containing the new bacterial strain and/or its derivatives.

The term derivative refers to spores and sporangia obtained from strain UNISS18 itself by use of well known culture and isolation methods, from strains derived by growth under mutagenic or selective conditions, as well as from strains obtained by genetic transformation with DNA sequences of various exogenous or endogenous origin. Sub-cellular fractions obtained by separation and/or cell lysis, as for instance parasporal inclusions, provided that properties characteristic of the original strain (insecticidal activity) are maintained, are also intended as strain derivatives.

Cellular extracts from totally or partially lysed bacterial cultures, strain lyophilised or fractions obtained by enzymatic or high-pressure treatment or by mild treatment with detergents, acids or bases are also intended as strain derivatives.

The insecticidal properties of *Brevibacillus laterosporus* have been especially shown against mosquito larvae (*Culex quinquefasciatus* and *Aedes aegypti*), *Simulium vittatum*, coleopters, nematodes, molluscs and Lepidoptera larvae. Parasporal inclusions especially active against mosquitos are produced under certain conditions.

The insecticidal activity can be observed also in the absence of inclusions.

The same applicants have shown for the first time the lethal and sublethal effects of specific *Brevibacillus laterosporus* strains against *Musca domestica* by laboratory experiments published in Ruiu et al., 2006.

However each of the different components (spores, sporangia, vegetative cells) of strain UNISS18, object of the present invention, shows a higher activity compared to other known strains. Such activity is measured as the ability to kill flies, with special reference to the time of action which, in similar conditions, is shorter than the time required with the strain described by Ruiu et al. 2006. Comparative activity data are reported in the Experimental Part, Example 2.

In particular, the *Brevibacillus laterosporus* strain NCIMB 41419 proved to be more effective for control of Dipters, especially of the species *Musca domestica*, in zootechnical environments. In addition to flies, it shows an activity higher than well known strains also on other types of Dipters, such as Brachycerus and Nematocerus, as for instance mosquitos (common mosquito: *Culex pipiens*, Anopheles: *Anopheles maculipennis*, Tiger mosquito: *Aedes albopictus*), horseflies and midges.

This broad spectrum of activity, together with the lack of pathogenicity in human (*Brevibacillus laterosporus* is classified as non pathogenic bacterium in human), makes strain UNISS18 and its derivatives particularly suitable for biological control of insects.

The process for preparation of the insecticidal composition/formulation essentially includes the following steps:

a) Inoculum of the bacterium in a culture medium and amplification in a rich culture medium (where a rich culture medium is a medium containing also amino acids and/or proteins, in addition to salts and a carbon source) according to methods well known in the art, as for instance in L-B broth, at a temperature ranging between 20° C. and 40° C., preferably ranging between 25° C. and 35° C., even more preferably between 28° C. and 32° C.; similar results can be obtained using different liquid or solid culture media according to well known methods;

b) growth of bacteria preferably until the stage of sporulation; this growth is usually spontaneous after a period of at least 24-48 hours incubation in rich culture medium at the preferred temperature range; similar results can be obtained using different liquid or solid culture media according to methods well known in the art; sporulation can be directly observed with the optical phase contrast microscope;

c) optional lysis and/or cell fractionation;

d) collection of spores, of vegetative cells of sporangia or their intermediate stages, for instance by centrifugation, preferably with sequential washings with sterile distilled water, as well known in the art, in order to remove the soluble components (see Example 1);

e) resuspension of the pellet of spores, vegetative cells or sporangia, or their intermediate preparations as obtained in step d), in water or in an aqueous buffer suited to obtain a suspension lacking contaminants and showing insecticidal activity.

In general, the so obtained product corresponding to the active principle is suitably formulated according to the intended use, directly mixing the pellet and/or suspension with the appropriate excipients and diluents.

As mentioned above, the insecticidal activity is also present in suspensions containing vegetative cells or sporangia: In fact, similar results can be obtained using bacteria at stages different from the spore stage (sporangia, vegetative cells) or intermediate stages.

Each developmental or growth stage can be obtained by synchronized bacterial culture that can be induced as it is well known in the art. The culture is stopped and bacteria are collected either when they are simultaneously in the vegetative phase, or when up to 100% of bacteria are in sporulated form, or when bacteria are in the form of sporangia or when they are in the various intermediate phases. By synchronized culture it is meant a culture wherein the bacteria of the bacterial population undergo simultaneous reproduction, therefore at a given moment the bacteria are in the same development or growth phase (vegetative cells, sporangia, spores, various intermediate phases).

Spores, sporangia and vegetative cells, or their mixtures containing active principles, can be further treated and/or fractionated prior to mixing in formulations. Said treatments or fractionations include for instance lysis and subcellular fractionation, partial extraction by physico-chemical (e.g. centrifugation) or biochemical (e.g. enzymatic) methods. The subcellular fractions obtained using strain UNISS18 and showing insecticidal activity are also included in the present invention.

Formulations can be of several types, depending on the intended use: they can be feeding baits or compositions for treatment of paddock or for treatment, for instance by irrigation or spraying, of small or wide areas, for instance of zootechnical areas.

They are preferably, but not necessarily, in the form of fluid paste which proves to be effective for the control of *Musca domestica* at both preimmaginal stage and adult stage, in zootechnical environments. Similar effectiveness can be obtained in other environments populated by the above-mentioned dipteran.

Other types of formulations comprise the UNISS18 strain (or its derivatives) as active principle alone or in combination with one or several different active principles (for instance fertilizers, micronutrient-releasing substances, chemical or biological insecticides, fungicides, nematodicides, etc.) at concentrations ranging between 0.01 and 99.9%. As it is well known in the art, compositions are prepared with liquid or solid excipients, or even excipients under the form of powder, by mixing homogeneously the active principle with solvents, surfactants or solid or powder vehicles.

According to the present invention, by active principle it is meant the strain *Brevibacillus laterosporus* UNISS18 deposited with number NCIMB 41419, and its above defined derivatives.

The insecticidal effect on adults can be obtained by use of feeding baits that incorporate the formulation containing *Brevibacillus laterosporus*, in order to obtain a final concentration of at least $1\times10^5$ spores and/or sporangia and/or vegetative cells/gm, more preferably ranging between $1\times10^6$ and $1\times10^{12}$ or more preferably ranging between $1\times10^7$ and $1\times10^{10}$ spores and/or sporangia and/or vegetative cells/gm, even though the mortality of larvae or adult insects reaches 100% in 24 and 48 hours, respectively, already at a concentration of $1\times10^9$ spores and/or sporangia and/or vegetative cells/gm. Feeding baits are preferably formulated such that they contain, in addition to *Brevibacillus laterosporus*, any type of attractive agent, for instance sugar, substances of proteinaceous nature, nitrogenous substances, pheromones.

Therefore the active principle contained in insecticidal formulations and in the baits, under the form of spores or sporangia or bacterial pellet or their derivatives, is generally present in the same concentration range defined above: an equivalent concentration is used in the case of derivatives or other components.

Within the above-mentioned concentration ranges related to insecticidal activity, higher concentrations allow a more immediate lethal effect, while lower concentrations result in a slower action.

Various examples of formulation for preparations of the bacterial strain UNISS18 and its derivatives according to the invention are well known to an expert in the field and comprise:

aqueous suspensions of capsules (microcapsules): this formulation applied to some insecticides makes possible both toxicological and environmental safety. The insecticidal active principle is encapsulated in microspheres of non-toxic and inert material, e.g. nylon, in aqueous suspension;

microgranular formulations: this formulation also termed hydrodispersible microgranules, is produced by agglomeration of the solid active principle with a system acting as moisturizing/dispersing system;

concentrated aqueous suspensions (SC): these formulations also termed: fluid paste (flowable) colloidal paste, liquid paste. The solid and insoluble active principle is finely micronized in aqueous suspension.

bioencapsulation, as for *Bacillus thuringiensis*. The active principle is encapsulated in devitalized cells of another microorganism, for instance yeast or bacteria, e.g. *Pseudomonas fluorescens*. The bio-engineering encapsulation procedure, termed Cell Cap, allows protection of the active principle or endotoxins from the degrading action of sun light, heat, water. Such biological protection confers to the formulate higher duration, steadier efficacy and improved storage time;

water-soluble bags, consisting of containers made of thin, quickly water-soluble plastic layer which completely isolates the active principle from the environment and the agricultural operator.

According to a further aspect, the invention relates to the use of strain UNISS18 for control of Dipterans, Brachycerus and Nematocers, more specifically of flies, mosquitos (common mosquito: *Culex pipiens*, Anopheles: *Anopheles maculipennis*, tiger mosquito: *Aedes albopictus*) of horseflies and midges.

The control of pre-immaginal stages is achieved by treating the organic substrate on which they develop. The insecticidal effect is independent from the mode of incorporation of the formulation containing *Brevibacillus laterosporus* in said developmental substrate. In this way, a significant dose- and concentration-dependent effect on reduction of larval development capacity and a general increase in mortality at the pre-immaginal stages are obtained. These techniques also include the use of a suitably formulated strain or its derivatives, of additives and/or supplements for feeding animals in zootechnical production with the resulting fecal release of bacterial residues.

Laboratory experimentation by toxicity tests, after ingestion of various fractions extracted from the bacterium, show that toxicity is a toxin-mediated process; therefore, the present invention includes all formulations containing the new *Brevibacillus laterosporus* strain UNISS18 under the form of vegetative cells and/or sporangia and/or spores and/or toxins extracted thereof and/or derivatives as defined above, which result in an insecticidal effect on *Musca domestica* larvae and/or adults in environments populated by this insect.

Therefore, according to a further aspect, the method of the invention relates also to prevention of Diptera infestation.

*Brevibacillus laterosporus* strain UNISS18, NCIMB n° 41419 and its derivatives can be stored in freeze-dried form or frozen in presence of glycerol at least at −20° C., or at room temperature in stab or Agar plate. Methods for bacterial storage, maintenance and growth are known in the art and are described for instance in: MacFaddin, J. F. 1985. Media for isolation, cultivation, identification, maintenance of medical bacteria. Williams & Wilkins, Baltimore, Md. Or additionally in: Ted R. Johnson, Christine L. Case, James G. Cappuccino, Natalie Sherman, Virginia Schurman, Janet Savage, 1999. Biology 201: Microbiology Laboratory Manual. Addison-Wesley edition.

Some of the embodiments of the invention, illustrated below, represent only examples and therefore are not exhaustive nor limiting of what has been described above.

EXPERIMENTAL PART

Example 1

*Brevibacillus laterosporus* Strain UNISS18 Isolation, Culture and Laboratory Bioassays

*Brevibacillus laterosporus* strain UNISS18 was isolated from a soil sample collected in central Sardinia (Italy). 1 gm of soil has been resuspended in 10 ml of 50 mM phosphate buffer pH 7.0 and vigorously shaken for 20 minutes by use of a mechanic stirrer. The so obtained suspension has been heated to 70° C. for 30 minutes in order to devitalize the vegetative bacterial forms. The suspension has been then used to inoculate Petri Dishes containing Nutrient Agar or CCY Agar. After 2 days of incubation at 30° C., single bacterial colonies were analysed by optical and electron microscopy. Single colonies of *Brevibacillus laterosporus* strain UNISS18 have been transferred in new Petri Dishes containing CCY Agar and incubated until complete sporulation (2-3 days). Single colonies with insecticidal activity have been resuspended in 1 ml of Nutrient Broth and 15% of glycerol and stored at −80° C.

*Brevibacillus laterosporus* strain UNISS18 has been cultured in medium based on Luria-Bertani (LB) broth at 30° C. with shaking at 200 rpm. The culture has been harvested by centrifugation (10,000 g) only after complete sporulation of the whole population, that was ascertained by direct observation by optical phase contrast microscopy. After 3 consecutive centrifugation-resuspension cycles (washing) in sterile distilled water, the pellet was resuspended in water to a concentration of $2 \times 10^9$ spores/gm.

The so obtained suspension has been administered to flies by incorporation into food at a final concentration of $1 \times 10^9$ (adults) and $0.8 \times 10^9$ (larvae) spores/gm. Under these conditions, 100% mortality was achieved within the subsequent 24 or 48 hours, for larvae and adults, respectively.

The same results have been obtained using purified suspensions of spores, sporangia or vegetative cells or mixtures of spores and/or sporangia and/or vegetative cells of *Brevibacillus laterosporus* strain UNISS18.

The three growth phases mentioned above can be obtained, as it is well known in the art, by synchronized bacterial culture in liquid culture medium and subsequent harvesting of the bacterial culture at the point when bacteria are in vegetative phase or under form of sporangia or spores.

Similar results can be obtained with non-synchronized bacterial cultures containing mixtures of the various growth stages: vegetative cells and/or sporangia and/or spores.

Similar results can be obtained using bacteria at intermediate stages between the stages mentioned above (spores, sporangia, vegetative cells).

Example 2

Comparison Between UNISS18 and Other *Brevibacillus laterosporus* Strains with Respect to the Efficacy on Adults Following the procedure and concentrations shown in example 1, adult flies have been administered with preparations of suspensions of *Brevibacillus laterosporus* strains ATCC 9141, ATCC 6456 and ATCC 64 provided by the *Bacillus* Genetic Stock Center, in part already known for their toxicity on other Dipters (Rivers et al., 1991), and with suspensions of the strain used by Ruiu et al. (2006), in comparison to strain UNISS18 NCIMB 41419 according to the present invention. The mortality values obtained after 72 h were 20% for ATCC strain 9141, 33% for ATCC strain 6456, 13% for ATCC strain 64, 50% for the strain used by Ruiu et al. (2006) and 100% for strain UNISS18.

Example 3

Baits for Adults Containing *Brevibacillus laterosporus* Strain UNISS18

A feeding bait based on a candy fruit containing saccharose and *Brevibacillus laterosporus* strain UNISS18, at a concentration of $2\times10^8$ spores/g, has been prepared in the laboratory and tested on *Musca domestica* adults, resulting in 100% mortality. When the same bait was administered in a zootechnical company, it succeeded in holding back the fly population to levels comparable to those detected in similar companies undergoing common treatments with chemical pesticides.

Example 4

Manure Treatments with a Formulation Containing *Brevibacillus laterosporus* Strain UNISS18

A fluid formulation based on a sporulated culture of *Brevibacillus laterosporus* strain UNISS18 at a concentration of $1\times10^8$ spores/g has been incorporated into manure samples which constituted the substrate for development of young stages of *Musca domestica*. This treatment caused an increased mortality of young stages that reached 60%, compared to other samples used as negative control.

Example 5

Use of a Formulation Containing *Brevibacillus laterosporus* Strain UNISS18 on Paddock in Zootechnical Companies Manure treatments similar to those described in example 4. have been performed in zootechnical companies. Using the formulation mentioned in example 4, suppression of development of young stages has been obtained by treatments with a dose of 2 l/m² of paddock, that is the area outside the animal stable where preimaginal fly stages develop (this area is populated by *Musca domestica* adults in order to feed on the animals or the manure and to lay eggs).

BIBLIOGRAPHY

1) Favret E M & Yousten A A (1985) Insecticidal activity of *Bacillus laterosporus*. Journal of Invertebrate Pathology 45: 195-203.
2) Laubach A C (1916) Studies on aerobic, sporebearing, non pathogenic bacteria. Spore bearing organism in water. Journal of Bacteriology 1: 505-512.
3) McCray A H (1917) Spore-forming bacteria in the apiary. Journal of Agricultural Research 8: 399-420.
4) Oliveira E J, Rabinovitch L, Monnerat R G, Passos L K, & Zahner V (2004) Molecular Characterization of *Brevibacillus laterosporus* and Itz Potential Use in Biological Control. Applied Environmental Microbiology 70: 6657-6664.
5) Orlova M V, Smirnova T A, Ganushkina L A, Yacubovich V Y & Azizbekyan R R (1998) Insecticidal Activity of *Bacillus laterosporus*. Applied Environmental Microbiology 64: 2723-2725.
6) Rivers D B, Vann C N, Zimmack H L, & Dean D H (1991) Mosquitocidal Activity of *Bacillus laterosporus*. Journal Invertebrate Pathology 58: 444-447.
7) Ruiu L, Delrio G, Ellar D J, Floris I, Paglietti B, Rubino S & Satta A (2006) Lethal and sublethal effects of *Brevibacillus laterosporus* on the housefly (*Musca domestica*). Entomologia Experimentalis et Applicata 118: 137-144.
8) Singer S (1996) The Utility of Morphological Group II *Bacillus*. Advance Applied Microbiology 42: 219-261.
9) Smirnova T A, Minenkova I B, Orlova M V, Lecadet M M & Azizbekyan R R (1996) The crystal-forming strains of *Bacillus laterosporus*. Research in Microbiology 147: 343-350.

The invention claimed is:

1. A *Brevibacillus laterosporus* bacterial strain deposited as N° NCIMB 41419 in NCIMB Ltd. Aberdeen, UK.

2. An insecticidal composition comprising as the active principle, the *Brevibacillus laterosporus* according to claim 1.

3. The composition according to claim 2 containing an amount of bacillus/spores of at least $1\times10^5$ spores and/or sporangia and/or vegetative cells/g.

4. The composition according to claim 3 wherein said concentration ranges from $1\times10^6$ to $1\times10^{12}$ spores/g.

5. The composition according to claim 2 wherein the active principle is combined with one or more other active principles and/or with excipients, diluents or liquid solvent, or solid or powder.

6. The composition according to claim 5 in fluid paste.

7. The composition according to claim 5 further comprising a substance chosen from the group of: sugar, substances of proteinaceous origin, nitrogenous substances and pheromones.

8. Feeding bait comprising the composition according to claim 7.

9. Feeding bait comprising as the active principle the *Brevibacillus laterosporus* according to claim 1.

10. A process for the preparation of an insecticidal composition comprising the following steps:
    a) inoculation of a *Brevibacillus laterosporus* N° NCIMB 41419 culture in a rich medium;
    b) growth of the bacterium in culture for at least 3 hours at a temperature ranging between 20° C. and 40° C.;
    c) optional lysis and/or cell fractionation;
    d) harvest of the fraction of cells, spores or sporangia or of the subcellular fraction, and washings;
    e) resuspension in suitable buffer.

11. The process according to claim 10 wherein step b) is performed for at least 20 hours at a temperature ranging between 25° C. and 35° C.

12. The process according to claim 10 further comprising the step of adding insecticidal excipients, solvents, surfactants or vehicles or the step of adding feed compositions to prepare feeding baits.

13. A method for the biologic control of Dipters, wherein zootechnical areas are treated with a biological control agent selected from the group consisting of:
    the *Brevibacillus laterosporus* strain according to claim 1,
    a composition comprising as the active principle, the *Brevibacillus laterosporus* strain according to claim 1, and
    a bait comprising as the active principle, the *Brevibacillus laterosporus* strain according to claim 1.

14. The method according to claim 13 wherein said Dipters are Brachycerus or Nematocers.

15. The method according to claim 13 wherein said Dipters are Brachycerus.

16. The method according to claim 15, wherein said Brachycerus is *Musca domestica*.

17. The method according to claim 14 wherein said Dipters are Nematocers selected from the group consisting of: common mosquito, *Culex pipiens, Anopheles, Anopheles maculipennis*, tiger mosquito, and *Aedes albopictis*.

18. The method according to claim 14 wherein said Dipters are horseflies, *Tabanus bovinus*, or midges.

19. The method according to claim 13 comprising an in field prevention of Dipters infestation.

* * * * *